United States Patent [19]
Mazurkewitz

[11] Patent Number: 6,088,157
[45] Date of Patent: *Jul. 11, 2000

[54] RELAY LENS FOR AN ENDOSCOPE

[75] Inventor: Anthony Mazurkewitz, New Fairfield, Conn.

[73] Assignee: Circon Corporation, Santa Barbara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/691,192

[22] Filed: Aug. 5, 1996

[51] Int. Cl.⁷ .................................................. G02B 23/00
[52] U.S. Cl. ............................................................ 359/434
[58] Field of Search ..................... 359/434, 435; 600/138, 160

[56] References Cited

U.S. PATENT DOCUMENTS

| | | | |
|---|---|---|---|
| 4,036,218 | 7/1977 | Yamashita et al. | 128/4 |
| 4,676,606 | 6/1987 | Takahashi | 359/754 |
| 4,693,568 | 9/1987 | Takahashi | 359/772 |
| 5,020,893 | 6/1991 | Karst et al. | 359/435 |
| 5,568,312 | 10/1996 | Horton | 359/435 |

FOREIGN PATENT DOCUMENTS

| | | | |
|---|---|---|---|
| 000411843 | 1/1974 | U.S.S.R. | 600/138 |

*Primary Examiner*—Cassandra Spyrou
*Assistant Examiner*—Mark A. Robinson
*Attorney, Agent, or Firm*—Bradley M. Ganz

[57] ABSTRACT

A relay lens for an endoscope or optical instrument is shown. The relay lens includes a first rod-type lens element having a first end and a second end. The first end defines a substantially spherical surface and the second end defines a convex surface. An optical element is positioned in axial alignment with and adjacent the first rod-type lens element. The optical element has a concave surface and a convex surface. The concave surface of the optical element is bonded to the convex surface of the second end of the first rod-type lens element forming a single bonded gap between the concave and convex surfaces. A second rod-type lens element having a first end and a second end, wherein each of the first end and second end defines a substantially spherical surface, is positioned in an axially aligned relationship with the first rod-type lens element and spaced from at least one of the first end of the first rod-type element and the concave surface of the optical element. A method of manufacturing a relay lens is also shown.

18 Claims, 2 Drawing Sheets

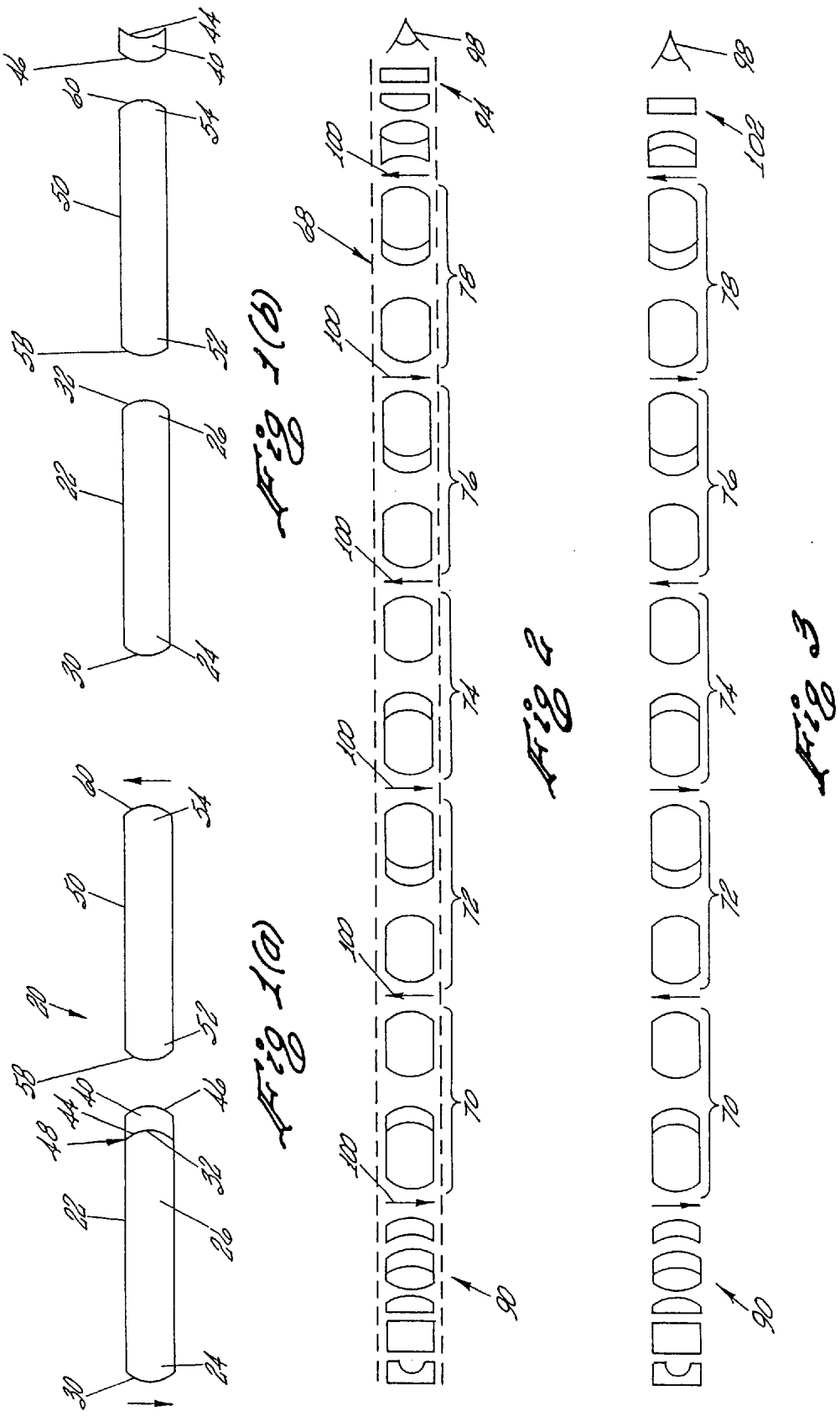

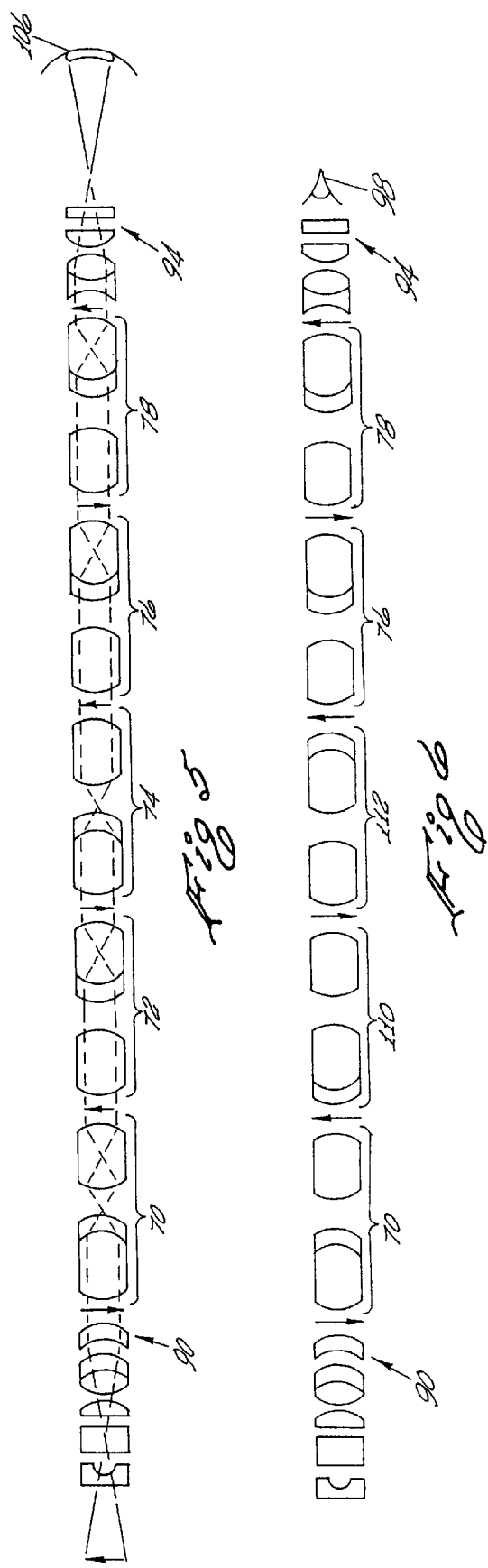

RELAY LENS FOR AN ENDOSCOPE

BACKGROUND OF THE INVENTION

1. Field of the Invention

This invention relates to an optical lens system for an instrument and more particularly relates to a lens relay which forms part of a lens relay system having a plurality of lens relays for a medical endoscope and wherein the medical endoscope is capable of withstanding an autoclaving process of sterilization in a medical environment.

2. Description of the Prior Art

The use of rod-type lens elements or elongated lens elements in an endoscope is well known. One well known lens relay system is described in U.S. Pat. No. 3,257,902 and is referred to as the "Hopkins" relay lens system. The "Hopkins" relay lens system transfers an optical image developed by an objective lens to an adjacent relay lens system or an eyepiece lens and achieves an acceptable level of transfer of a high brightness image with correction of optical aberrations. The "Hopkins" relay lens system uses a combination of bi-convex rod-type lens and meniscus lens. A typical "Hopkins" relay lens system has two cemented or bonded gaps per relay lens. A medical endoscope uses a plurality of "Hopkins" relay lens system. Therefore, there can be as many as 13 cemented or bonded gaps per endoscope.

U.S. Pat. No. 5,005,960 discloses a relay lens system having four optical elements in symmetrical arrangement. In the relay lens system of U.S. Pat. No. 5,005,960, two rod type lens elements and two convex/concave optical elements are used with one rod system lens and one further lens, all of which are bonded to each other. Thus two cemented or bonded gaps are required for each relay lens.

Another known endoscope relay is disclosed in U.S. Pat. No. 5,059,009. The relay lens disclosed in U.S. Pat. No. 5,059,009 includes two identical end lenses affixed to opposed ends of a center lens to define a cylinder. The relay lens is symmetrical about a plane bisecting the center of the center lens. The axial length of each end lenses is equal to or greater than one-half its diameter. Each end lens has one end connected to the center lens. Thus, each relay lens has two cemented gaps or four adhesive-glass surfaces for each relay lens.

SUMMARY OF THE PRESENT INVENTION

The present invention discloses a novel, unique and improved relay lens for an endoscope or instrument. In the preferred embodiment, the relay lens is used in an autoclavable medical endoscope. Typically a plurality of relay lens forming a relay lens system are used in the endoscope, and the number thereof is usually determined by the length of the endoscope.

In the present invention, the relay lens for an endoscope includes a first rod-type lens element having a first end and a second end. The first end defines a substantially spherical surface and the second end defines a convex surface. An optical element is positioned in axial alignment with and adjacent the first rod-type lens element. The optical element has a concave surface and a convex surface. The optical element has the concave surface bonded to the convex surface of the second end of the first rod-type lens element forming a single bonded gap between the concave and convex surfaces. A second rod-type lens element, having a first end and a second end, wherein each of the first end and second end defines a substantially spherical surface, is positioned in an axially aligned relationship with the first rod-lens element and optical element. The second rod-type lens element is spaced from at least one of the first end of the first rod-type element and the concave surface of the optical element. In the preferred embodiment, second rod-type lens element is positioned with one of the first end and second end spaced from the convex surface of the optical element.

Certain problems are associated with the known prior art relay lens. Such problems include, without limitation, that medical endoscopes having a plurality of relay lenses include a large number of cemented gaps. When such a medical endoscope is subjected to an autoclavable process of sterilization in a medical environment, the cemented gaps experience detrimental effects in optical transmission properties. Since a medical endoscope includes a plurality of relay lenses each having numerous cemented gaps, the total number of cemented gaps in a medical endoscope depends directly on the number of relay lenses utilized in the medical endoscope. In a medical environment, a medical endoscope having a plurality of relay lenses each having numerous cemented gaps are sterilized in an autoclaving process which subjects the medical endoscope, including the cemented gaps, to high temperatures and pressures, for prolonged periods of time. The known medical endoscopes having a large number of cemented gaps, when continuously subjected to such high temperatures and pressures, degrade in optical transmission performance, quality, color and brightness due to the cemented gaps transmission properties being degraded by the autoclaving process of sterilization.

Medical endoscopes, as a surgical instrument, require sterilization before each procedure. As such, medical endoscopes are cycled through hundreds of autoclavable sterilization processes or cycles during the normal useful life of the endoscope or instrument. Also the medical endoscope and instruments are subject to other sterilization processes exposing the medical endoscope to at least one of high temperatures, high pressures, caustic cleaning solutions, disinfectant and the like.

Such sterilization procedures have a detrimental effects on the ability of the medical endoscope to transfer optical images by degrading the transmission and/or reflection properties of the cement or adhesion material used to cement or bond the elements of each relay lens.

It is readily apparent that as the number of cemented gaps used in a medical endoscope is increased, the corresponding cumulative effect of the autoclaving process of sterilization on a large number of cemented gaps results in a significant reduction in the transmission characteristics of the endoscope or instrument. The reduction in transmission characteristic occurs because of the aggregate reduction in the color and transmission of the image in each of the cement gaps individually.

In the optical design of a relay lens, it is desirous to have simplicity in the formulation of the relay lens so as to keep the cost of production of the relay lenses at an economical level. Simultaneously, it is desirous to minimize the number of adhesive-glass surfaces as well as the number of air-glass surfaces, per relay lens, so as to maintain the correct color of the optically transferred image. Reflections occurring at air-glass surfaces tend to alter the color of the final image and subtract from the total light transmission even with the use of anti-reflection coatings on these surfaces. Endoscopes normally contain many air-glass surfaces as several relay lenses are used in a relay lens system to transfer the image to the proximal end of the endoscope or instrument.

Therefore, one advantage of the present invention is that the number of cemented gaps in a relay lens is minimized to one per relay.

Another advantage of the present invention is that an endoscope or instrument utilizing a plurality of relay lenses each having a single cemented gap will have good optical image transmission properties over the life of the instrument, particularly if the endoscope or instrument is repeatedly subject to an autoclaving process of sterilization.

Another advantage of the present invention is that the simplicity in optical design keeps the cost of production of relay lenses and of the instrument including medical endoscopes using such relay lenses at an economical level.

Another advantage of the present invention is that a reduction in both the number of air-glass surfaces per relay lens and cement-glass gaps per relay enables the instrument to better maintain the correct color of the optically transferred image transmitted from the distal end to the proximal end of the endoscope or instrument.

Another advantage of the present invention is that a medical endoscope comprising a relay lens system having a plurality of relay lenses of the present invention can be cycled through numerous sterilization cycles including the autoclaving sterilization process in a medical environment without a significant reduction in optical transmission properties of the endoscope over the typical life of an endoscope.

Another advantage of the present invention is that the relay lens of the present invention has one cemented gap forming two cement-glass surfaces and all of the remaining surfaces have air-glass surfaces.

Another advantage of the present invention is that a novel method of manufacturing a relay lens of the present invention is disclosed and taught hereon.

BRIEF DESCRIPTION OF THE DRAWINGS

The features, aspects and advantages of the present invention will be readily apparent when considered in light of the following description hereinafter, including the description of the preferred embodiment, and the drawing set forth herein which includes the following figures, all of which are presented by way of example only, and not of limitation, and all obvious modifications hereof are understood to be part of or within the scope of the disclosure set forth herein:

FIG. 1(a) is a pictorial representation of one embodiment of a relay lens of the present invention;

FIG. 1(b) is a pictorial representation of a first rod-type lens element, a second rod-type lens element and an optical element comprising the various elements of the relay lens of the present invention;

FIG. 2 is a diagrammatic representation of a medical endoscope utilizing a plurality of relay lenses forming one embodiment of a relay lens system of the present invention with one embodiment of an objective lens and one embodiment of an eye lens for forming an image in an eye;

FIG. 3 is a diagrammatic representation of a medical endoscope utilizing a plurality of relay lenses forming the same embodiment of a relay lens system of FIG. 2 with the same embodiment of an objective lens illustrated in FIG. 2 and another embodiment of an eye lens for forming an image in an eye;

FIG. 4 is a chart of certain criteria for a single relay lens and a relay lens system having five relay lens;

FIG. 5 is a diagrammatic representation of a medical endoscope utilizing a plurality of relay lenses forming the same embodiment of a relay lens system of FIG. 3 with the embodiment of an objective lens illustrated in FIG. 2 and an eye lens of the embodiment of FIG. 2 for forming an image for an image receiving means; and FIG. 6 is a diagrammatic representation of a medical endoscope utilizing a plurality of relay lenses forming another embodiment of a relay lens system of the present invention with the embodiment of an objective lens illustrated in FIG. 2 and the embodiment of the eye lens shown in FIG. 5 for forming an image in an eye.

DESCRIPTION OF THE PREFERRED EMBODIMENT

The relay lens of the present invention is adapted for use in optical instruments having an elongated shaft or housing. In the preferred embodiment of the present invention, the relay lens is the basic element of a relay lens system comprising a plurality of separate relay lenses.

The structure of the preferred embodiment is utilized in a medical endoscope which is a surgical instrument or medical device used for visualization of an operative site within the human body or a cavity located within the human body. In a medical environment, medical endoscopes are cleaned, disinfected and sterilized prior to use in a surgical procedure. The primary type of surgical procedures in which medical endoscopes are utilized are generally referred to as "minimally invasive surgery".

In using surgical instruments including medical endoscopes, there is an increased concern and awareness about the possibility of transferring infectious diseases, such as for example Hepatitis B and AIDS, between patients. As such, the present procedures for sterilizing surgical instruments now require that such instruments be thoroughly cleaned, disinfected and sterilized between procedures to insure that any infectious disease or other material has been removed or destroyed by an effective sterilization procedure.

In the present medical environment, a number of known sterilization systems, sterilization fluids and pressurized sterilization techniques are used to insure effective sterilization of the surgical instrument including medical endoscopes. Such systems, fluid and techniques are well known in the art and need not be discussed in detail herein.

The use of an autoclaving process for sterilization of medical instruments is the preferred sterilization procedure and technique. This is due to the reliability of high temperatures and pressures used in the autoclaving process over a sterilization cycle to effectively sterilize surgical instruments including medical endoscopes.

Thus, in the preferred embodiment of the present invention, the relay lens and a relay lens systems comprising a plurality of relay lenses are used in a medical endoscope which can survive hundreds of autoclaving sterilization processes without having an adverse or detrimental effect on the optical transmission characteristics of the medical endoscope during the useful life of the endoscope.

Although the preferred embodiment of the relay lens and a relay lens system using the relay lens of the present invention is adapted for use in an autoclavable medical endoscope, such relay lens can be used for other optical instruments such as, without limitation, borescopes, cystoscopes, hysteroscopes, resectoscopes, thoracoscopes and the like. The use of the term "endoscope" or the term "instrument" is not intended to be limiting and is being used as a generic term without any limitation of the applicability or use of the present invention in an optical device or the environment in which such endoscopes or instruments are used.

Referring to FIG. 1(a), the basic relay lens, shown generally as 20, is adapted for use in an endoscope or instrument. The relay lens 20 includes a first rod-type lens element 22 having a first end 24 and a second end 26. This structure is sometimes referred to herein as a pair of ends.

The first end 24, or one of the pair of ends, defines a substantially spherical surface 30 and the second end 26, or the other of the pair of ends, defines a convex surface 32. As is apparent from FIG. 1(a), the first rod-type lens element 22 is generally in the form of a first elongated lens element with a rod-type structure being the preferred embodiment. The first elongated lens element can have any predetermined cross sectional geometry that is suitable for use with the optical instrument in which it is to be used. For example, the predetermined cross-sectional geometry can be a circle, a square, a rectangle, an oval or other geometric structure. Typically, the structure is determined by the structure and/or cross sectional area of an elongated shaft or housing of an endoscope or instrument into which the relay lenses are to be assembled or used.

An optical element 40 is positioned in axial alignment with and adjacent the first rod-type lens element 22. The optical element 40 has a concave surface 44 and a convex surface 46. In the embodiment illustrated in FIG. 1(a), the optical element 40 has the concave surface 44 bonded to the convex surface 32 of the first rod-type lens element 22 forming a single bonded gap shown generally by arrow 48 between the convex surface 32 and the concave surface 44.

The bonding of the optical element 40 to the first rod-type lens element 22 can be performed by use of known bonding techniques which may include thermally responsive, optically transparent bonding materials. In the preferred embodiment, the bonding step utilizes a bonding material or a optical adhesive which preferably is a optical cement. Optical cements are well known to those skilled in the art. Known optical cements which are suitable as a bonding material for practicing this invention include LOCTITE® ultraviolet curing adhesive 353 offered for sale and sold by the Industrial Group of Loctite Corporation. Another known optical adhesive which can be used for practicing this invention is a polymer system UV10 adhesive sold under the trademark UV10 Medical by Master Bond, Inc.

FIG. 1(a) illustrates that the relay lens 20 further includes a second rod-type lens element 50 having a first end 52 and a second end 54. This structure is sometimes referred to herein as a pair of ends. The second rod-type lens element 50 is likewise an elongated lens element and could have a structure and/or cross sectional area as described hereinabove with respect to the first rod-type lens element 22.

In the preferred embodiment, the second rod-type lens element 50 has each of its first end 52 and second end 54 defining a substantially spherical surface 58 and 60, respectively. As illustrated in the embodiment of FIG. 1(a), the second rod-type lens element 50 is positioned in an axially aligned relationship with the first rod-type lens element 22 and the optical element 40. The second rod-type lens element 50 has its substantially spherical surface 58 of the first end 52 spaced from the convex surface 46 of the optical element 40. This is one structure for the relay lens 20.

Another structure for the relay lens 20, which is illustrated in and discussed in FIG. 6 with respect to relay lens 110 and 112, is where the second rod-type lens element 50 is positioned in an axially aligned relationship with the first rod-type lens element 22 and optical element 40 with one of the substantially spherical surfaces 58 or 60 spaced from the substantially spherical surface 30 of the first rod-type lens element 22.

FIG. 1(b) illustrates pictorially that the relay lens element 20 comprises three elements namely, a first elongated lens element 22, an optical element 40 and a second elongated lens element 50. Of course, the convex surface 32 of the first end 26 of the first elongated lens element 22 is bonded to the concave surface 44 of the optical element 40 making the first elongated lens element 22 and the optical element 40 an integral optical element.

In the preferred embodiment, the substantially spherical surfaces are spherical surfaces having a predetermined radii. In addition, at least one of the substantially spherical surfaces of the optical elements can be altered slightly to form an aspheric surface in order to reduce spherical aberrations.

In the preferred embodiment, the first and second rod-type lens element and the optical element are formed of a glass material. One example of a optical glass material that can be used in the forming of the first and second rod-type lens element and the optical element is BK7 and SF5 offered for sale and sold by Schott Optical Glass. In the alternative, the first and second rod-type lens element and the optical element can be formed of plastic material. One example of plastic materials that can be used in the forming of the first and second rod-type lens element and the optical element is Plexiglas and Styron offered for sale and sold by Rohm & Hass.

FIG. 2 illustrates an autoclavable medical endoscope having an elongated shaft or housing shown by dashed lines 68 for receiving all of the optical elements forming the optical image transferring means of the medical endoscope. As illustrated in FIG. 2, the relay lens system includes five separate relay lenses 70, 72, 74, 76 and 78. The structure of the embodiment of the lens relay system shown in FIG. 2 is that each of the relay lenses 70 through 78 has an orientation as depicted in FIG. 1(a).

In a typical medical endoscope and as illustrated in FIG. 2, an objective lens shown generally as 90 is located at the distal end of the elongated shaft 68 and an eye lens shown generally as 94 is generally located at the proximal end of the elongated shaft 68. The eye lens 94 forms an image for the eye 98. The image is transferred from the objective lens 90, through each of the relay lenses 70 through 78 to the eye lens 94. Arrows 100 show the orientation of the image at various stages within the relay lens system.

In the diagrammatic representation of a medical endoscope in FIG. 3, the medical endoscope utilizes a plurality of relay lenses 70 through 78 forming the same embodiment of a relay lens system of FIG. 2 with the same embodiment of an objective lens 90 illustrated in FIG. 2. In FIG. 3, another embodiment of an eye lens 102 is shown which is utilized for forming an image in the eye 98.

In the chart of FIG. 4, a comparison is made between the characteristics including the number of cement-gaps and air-glass surfaces for a single relay lens and a relay lens system having five relay lens. The first column labeled "System Parts" shows that the single relay lens has 3 elements while the relay lens system having 5 relay lens has 15 elements.

In the second column labeled "Spherical Surfaces", the chart shows that the single relay lens has 6 spherical surfaces while the relay lens system having 5 relay lenses has 30 spherical surfaces.

In the third column labeled "Plano Surfaces", the chart shows that both the single relay lens and the relay lens system having 5 relay lens has 0 plano surfaces.

In the fourth column labeled "Cemented Gaps", the chart shows that the single relay lens has 1 cemented gap while the relay lens system having 5 relay lenses has 5 cemented gaps. Thus, the single cemented gap results in two cemented surfaces.

In the fifth column labeled "Glass/Air Surfaces", the chart shows that the single relay lens has 4 glass/air surfaces while the relay lens system having 5 relay lenses has 20 glass/air surfaces.

In the diagrammatic representation of a medical endoscope in FIG. 5, the medical endoscope utilizes a plurality of relay lenses 70 through 78 forming the same embodiment of a relay lens system of FIG. 2. Also, the same embodiment of an objective lens 90 illustrated in FIG. 2 is used and the same embodiment of the eye lens 94, which is the same embodiment illustrated in FIG. 2, is utilized for forming an image. The image is focused on image receiving means 106. The image receiving means 106 may be an eye, a CCD Sensor, a video camera, a film camera or any other type of optical device for generating an optical image or generating an electronic image which can be processed by a video image processor or the like.

FIGS. 2, 3 and 5 illustrate embodiments of a lens relay system having at least three relay lenses 70, 76 and 78 wherein each of the second rod-type lens elements 50, illustrated in FIG. 1(a), are positioned with one of the pair of ends spaced from the convex surface 46 of its associated optical element 40, as illustrated in FIG. 1(a). In addition, in the embodiments of FIGS. 2, 3 and 5, the lens relay system has two additional relay lens 72 and 74 which have the same orientation as the relay lens 70, 76 and 78.

In the diagrammatic representation of the medical endoscope in FIG. 6, the medical endoscope utilizes a plurality of relay lenses forming another embodiment of a relay lens system. Specifically, the medical endoscope illustrated in FIG. 6 has three relay lenses 70, 76 and 78 which are of the same orientation as the relay lens illustrated in FIG. 5. However, relay lens 110 and 112 have a different orientation than relay lens 72 and 74 of FIG. 5. specifically, the relay lens 110 and 112 have the second rod-type lens element 50, illustrated in FIG. 1(b), in a different orientation than diagrammatically illustrated in FIG. 1(a). One of the substantially spherical surfaces 58 and 60 of the second rod-type lens element 50 is spaced from the substantially spherical surface 30 of the first rod-type lens element 22. Thus, the relay lens system in the embodiment illustrated in FIG. 6 has at least two relay lens wherein each of the second rod-type lens elements are positioned with one of the pair of ends having the substantially spherical surfaces spaced from the substantially spherical surfaces of the first end of the first rod-type lens element.

In addition, the medical endoscope of FIG. 6 has an objective lens 90 which is similar to the objective lens structure of FIGS. 2, 3 and 5 and an eye lens 94 which is similar in structure to the eye lens 94 as illustrated in FIGS. 2 and 5. The eye lens 94 in FIG. 6 forms an image for the eye 98.

TABLE A sets forth below, for an endoscope having the first rod-type lens element, the second rod-type lens element and the optical element all formed of glass material, the numerical values of the surface radii, the lens thickness (excluding air gaps) between these surface radii, and the refractive indices, together with the Abbe numbers for the d-line of the glass material.

TABLE A

| Surface Referenced FIG. 1(a) | Radius, mm. | Thickness, mm | Refractive Index | Abbe Number |
|---|---|---|---|---|
| 30 | 15.43 | 43.4 | 1.520 | 64.2 |
| 32 | −7.58 | 1.0 | 1.673 | 32.2 |
| 46 | −15.83 | 0.5 | | |
| 58 | 15.43 | 45.1 | 1.520 | 64.2 |
| 60 | −15.43 | | | |

TABLE B sets forth below, for an endoscope having the first rod-type lens element, the second rod-type lens element and the optical element all formed of plastic material, the numerical values of the surface radii, the lens thickness (excluding air gaps) between these surface radii, and the refractive indices, together with the Abbe numbers for the d-line of the plastic material.

TABLE B

| Surface Referenced FIG. 1(a) | Radius, mm. | Thickness, mm | Refractive Index | Abbe Number |
|---|---|---|---|---|
| 30 | 14.90 | 43.7 | 1.492 | 57.4 |
| 32 | −6.87 | 1.0 | 1.591 | 30.9 |
| 46 | −16.34 | 0.1 | | |
| 58 | 14.90 | 45.2 | 1.492 | 57.4 |
| 60 | −14.90 | | | |

TABLE C sets forth below, for an endoscope having the first rod-type lens element and the second rod-type lens element formed of a glass material and the optical element formed of a plastic material wherein the plastic material is in the form of a aspheric plastic meniscus lens having aspheric described by an equation of an aspheric formula labeled FORMULA F-1 set forth below, the numerical values of the surface radii, the lens thickness (excluding air gaps) between these surface radii, and the refractive indices, together with the Abbe numbers for the d-line for the applicable glass material and plastic material.

TABLE C

| Surface Referenced FIG. 1(a) | Radius, mm. | Thickness, mm | Refractive Index | Abbe Number |
|---|---|---|---|---|
| 30 | 15.40 | 43.8 | 1.520 | 64.2 |
| 32 | −8.27 | 1.0 | 1.591 | 30.9 |
| *46 | −18.97 | 0.1 | | |
| 58 | 15.40 | 45.1 | 1.52 | 64.2 |
| 60 | −15.40 | | | | wherein the aspheric of the of the aspheric plastic meniscus lens is described by the following equation of FORMULA F-1:

FORMULA F-1

$$*Z = \frac{ch^2}{1+\sqrt{1-(1+k)c^2h^2}} + Ah^4 + Bh^6 + Ch^8 + Dh^{10}$$

wherein:

$Z$ = sagitta of surface parallel to $z$ axis $c$ = curvature of surface = $\frac{1}{R}$ $k$ = conic coefficient, $k = 0$ (sphere)

$A$, $B$, $C$ and $D$ = 4th, 6th, 8th and 10th order deformation coefficients, respectively.

$h$ = Maximum radial distance measured orthogonally from the optical axis to any point on the surface.

In the example utilized in Table C, the following values were utilized for A, B, C, D and K:

$A = 0.1477E - 04$
$B = 0.3306E - 07$
$C = 0$
$D = 0$
$K = 0$ (sphere)

Depending upon the material and application, the numerical values for the 4th, 6th, 8th and 10th order deformation coefficients, respectively, can be selected in accordance with parameters as determined by those skilled in the art.

It is anticipated that in the relay lens system of the present invention each of the first and second rod-type element and the optical element can be formed of one of a glass material and a plastic material. For example, the first rod-type element could be formed of glass, the second rod-type lens element could be formed of plastic and the optical element could be formed of either glass or plastic material. In the alternative it is apparent to those skilled in the art that any combination of glass and plastic material could be utilized in practicing this invention.

A method of manufacturing a relay lens using the teachings of the present relay lens can be performed as follows. The method comprises the steps of: (a) forming a first thin rod-type lens element having a pair of ends wherein one of the pair of ends defines a substantially spherical surface and the other of the pair of ends defines a convex surface; (b) forming an optical element having a concave surface and an opposed convex surface; (c) bonding the concave surface of the optical element with a bonding material to the convex surface of the other of the pair of ends of the first rod-type lens element forming a single bonded gap between the concave and convex surfaces; (d) forming a second thin rod-type lens element having a pair of ends wherein each of the pair of ends defines a substantially spherical surface; and (e) assembling the second rod-type lens element in an axially aligned relationship with the first rod-type lens element and optical element with one of the pair of spherical surfaces of the second rod-type lens element in an opposed spaced relationship with at least one of a spherical surface of the first rod-type lens element and the convex surface of the optical element.

The method can include additional steps in accordance with the disclosure set forth above.

For reasons inherent in the production process, it may be necessary to use several elements, e.g. an elongated cylindrical element, a planoconvex and a planoconcave element, both with ends bonded for fixing and made of the same glass material or appropriate plastic material, to assemble the rod-type lenses. Lens systems comprising glass lenses, plastic lenses or a combination of glass lenses and plastic lenses made in such a way will, of course, come within the teachings of the present invention including the scope of protection covered by the foregoing claims.

A person skilled in the art can select the specific properties of the elements depending on the endoscope parameters, and the above ranges set forth in Tables A through C are for various embodiments and are not limiting. The use of a single bonded gap forming adhesive-glass surfaces and the other surfaces being glass-air surfaces provide a relay lens structure that enables the color, quality and brightness of the optical image transferred by the relay lenses to relayed with minimum absorption. The optical cement, when exposed to high temperature and pressure of an autoclaving sterilization process, particularly when the instrument is cycled through a plurality of autoclaving sterilization processes, exhibits minimum changes over a period of time substantially equal to the life of the endoscope or instrument. In the preferred embodiment of an autoclavable endoscope utilizing the lens relay disclosed herein; the bonding material, glass material and plastic material are selected to withstand temperatures and pressures of an autoclaving process without substantially affecting the optical characteristics thereof. As such, the color, quality and brightness of the optical image will remain in a highly acceptable range of use.

What is claimed is:

1. A relay lens for an endoscope comprising
a first rod-type biconvex lens element having opposing convex ends and a single bond interface separating the lens element into two portions in axial alignment with each other, each portion having a different refractive index;
a second rod-type lens element in an axially aligned, spaced apart relationship with the first rod-type lens element, the second rod-type lens element having no bond interfaces; and
the first and second lens elements defining a relay lens, the relay lens having only four air-glass surfaces and being capable of receiving an image at one end and producing an inversion of the image at the other end at about unit magnification.

2. The relay lens of claim 1 wherein the first portion of the first lens element is a biconvex lens and the second portion is a concave-convex lens with the concave end being bonded to a convex end of the first portion.

3. The relay lens of claim 2 wherein the convex end of the second lens element is in an axially aligned, spaced apart relationship with the convex end of the second portion of the first rod-type lens element.

4. The relay lens of claim 1 wherein the second lens element has a uniform refractive index.

5. The relay lens of claim 1 wherein the second lens element has a different length between end surfaces than the first lens element.

6. A lens for an endoscope comprising
a first rod-type biconvex lens element having opposing convex ends and a single bond interface separating the lens element into two portions in axial alignment with each other, each portion having a different refractive index, the first portion being a biconvex lens and the second portion being a concave-convex lens, the concave end being bonded to a convex end of the first portion;
a second rod-type lens element in an axially aligned, spaced apart relationship with the first rod-type lens element, the second rod-type lens element having a different length between end surfaces than the first lens element and a uniform refractive index, the uniform refractive index being different than the refractive index of at least the first or second portion of the first lens element; and the first and second lens elements defining a relay lens having only four air-glass interfaces, the relay lens being capable of receiving an image at one end and producing an inversion of the image at the other end at about unit magnification.

7. An endoscope comprising:

an objective lens; an eye lens; and a plurality of relay lenses axially aligned between the objective lens and eye lens; at least one relay lens comprising:

(a) a first rod-type biconvex lens element having opposing convex ends and a single bond interface separating the lens element into two portions in axial alignment with each other, each portion having a different refractive index;

(b) a second biconvex rod-type lens element in an axially aligned, spaced apart relationship with the first rod-type lens element, the second rod-type lens element having no bond interfaces; and (c) the first and second lens elements defining a relay lens having only four air-glass surfaces and a single bond interface, the relay lens being capable of receiving an image at one end and producing an inversion of the image at the other end at about unit magnification.

8. The endoscope of claim 7 wherein the first portion of the first lens element is a biconvex lens and the second portion is a concave-convex lens with the concave end being bonded to a convex end of the first portion.

9. The endoscope of claim 8 wherein the convex end of the second lens element is in an axially aligned, spaced apart, relationship with the convex end of the second portion of the first rod-type lens element.

10. The endoscope of claim 9 wherein the second lens element has a uniform refractive index.

11. The endoscope of claim 7 wherein the endoscope includes at least three relay lenses comprising:

(a) a first rod-type biconvex lens element having opposing convex ends and a single bond interface separating the lens element into two portions in axial alignment with each other, each portion having a different refractive index, the first portion being a biconvex lens and the second portion being a concave-convex lens, the concave end being bonded to a convex end of the first portion;

(b) a second rod-type lens element in an axially aligned, spaced apart relationship with the first rod-type lens element, the second rod-type lens element having a different length between end surfaces than the first lens element and a uniform refractive index, the uniform refractive index being different than the refractive index of at least the first or second portion of the first lens element; and (c) the first and second lens elements defining a relay lens, the relay lens being capable of receiving an image at one end and producing an inversion of the image at the other end at unit magnification.

12. A relay lens for an endoscope comprising:

a first rod-type biconvex lens element having opposing convex ends and a single bond interface separating the lens element into two portions in axial alignment with each other, each portion having a different refractive index;

a second rod-type biconvex lens element in an axially aligned, spaced apart relationship with the first rod-type lens element, the second rod-type lens element having a uniform refractive index, the refractive index being different from the refractive index of at least the first or second portion of the first lens element; and the first and second lens elements defining a relay lens, the relay lens being capable of receiving an image at one end and producing an inversion of the image at the other end at about unit magnification;

wherein the first portion of the first lens element is a biconvex and the second portion is a concave-convex lens with the concave end being bonded to a convex end of the first portion.

13. The relay lens of claim 12 wherein the convex end of the second lens element is in an axially aligned, spaced apart relationship with the convex end of the second portion of the first rod-type lens element.

14. The relay lens of claim 13 wherein the second rod-type lens element has no bond interfaces so that the single bond interface separating the first rod-type lens element into two portions is the only bond interface in the relay lens.

15. An endoscope comprising:

an objective lens; an eye lens; and a plurality of relay lenses between the objective lens and eye lens; at least one relay lens comprising:

a first rod-type biconvex lens element having opposing convex ends and a single bond interface separating the lens element into two portions in axial alignment with each other, each portion having a different refractive index;

a second rod-type biconvex lens element in an axially aligned, spaced apart relationship with the first rod-type lens element, the second rod-type lens element having a uniform refractive index, the uniform refractive index being different from the refractive index of at least the first or second portion of the first lens element;

the first and second lens elements defining a relay lens the relay lens being capable of receiving an image at one end and producing an inversion of the image at the other end at about unit magnification; and wherein the first portion of the first lens element is a biconvex lens and the second portion is a concave-convex lens with the concave end being bonded to a convex end of the first portion.

16. The endoscope of claim 15 wherein the convex end of the second lens element is in an axially aligned, spaced apart relationship with the convex end of the second portion of the first rod-type lens element.

17. The endoscope of claim 16 wherein the second rod-type lens element has no bond interfaces so that the single bond interface separating the first rod-type lens element into two portions is the only bond interface in the relay lens.

18. The endoscope of claim 17 wherein the second lens element has a different length between end surfaces than the first lens element.

* * * * *